United States Patent [19]  [11]  4,411,802
Lester et al.  [45]  Oct. 25, 1983

[54] ENHANCED OIL RECOVERY

[75] Inventors: George W. Lester, Hoffman Estates; Thomas P. Malloy, Lake Zurich, both of Ill.

[73] Assignee: UOP Inc., Des Plaines, Ill.

[21] Appl. No.: 299,708

[22] Filed: Sep. 8, 1981

[51] Int. Cl.$^3$ ............................................. E21B 43/22
[52] U.S. Cl. ............................... 252/8.55 D; 166/275; 260/505 C
[58] Field of Search ............... 252/855 D; 260/505 C; 166/275

[56]  References Cited

U.S. PATENT DOCUMENTS

| 2,227,999 | 1/1941 | Brandt et al. | 260/505 |
| 3,508,611 | 4/1970 | Davis et al. | 252/8.55 |
| 3,970,690 | 7/1976 | Suzuki et al. | 260/505 |
| 3,981,361 | 9/1976 | Healy | 252/8.55 X |
| 4,008,165 | 2/1977 | Maddox, Jr. et al. | 252/8.55 |
| 4,013,569 | 3/1977 | Chiu et al. | 252/8.55 |
| 4,058,467 | 11/1977 | Sias | 252/8.55 |
| 4,110,229 | 8/1978 | Carlin et al. | 252/8.55 |
| 4,214,999 | 7/1980 | Carlin et al. | 252/8.55 |

Primary Examiner—Herbert B. Guynn
Attorney, Agent, or Firm—James R. Hoatson, Jr.; Raymond H. Nelson; William H. Page, II

[57]  ABSTRACT

The recovery of residual oil which is found in subterranean reservoirs may be accomplished by utilizing an aqueous surfactant slug to reduce the interfacial tension between the oil and water. A surfactant slug which may be used will comprise a mixture of a neutralized sulfonate derivative from powdered coal, a lower alkyl alcohol which possesses from about 3 to about 6 carbon atoms and a non-ionic surfactant comprising an ethoxylated n-alcohol possessing from about 12 to about 15 carbon atoms. The surfactant slug will possess relatively low interfacial tension which may be in the range of from below $10^{-3}$ dynes per cm.

9 Claims, No Drawings

ENHANCED OIL RECOVERY

BACKGROUND OF THE INVENTION

It is well known in the petroleum field that petroleum which is found in subterranean reservoirs is recovered by many different methods. The primary method of petroleum recovery is by the primary recovery means which employs natural forces such as pressure, either by the petroleum itself or by the presence of gases, whereby petroleum is forced from the subterranean reservoir to the surface and recovered. Subsequent to the recovery of the etroleum by the primary means, due to the dissipation of the matural or gaseous pressure, more of the petroleum in the reservoir may be recovered by a secondary process in which water is forced into the reservoir to provide the pressure necessary to force the petroleum from the reservoir to the surface.

At some point in the recovery of petroleum, a state is reached in which it is more costly to use the water pumped in relative to the amount of oil which is recovered by this method. However, inasmuch as a relatively large amount of petroleum may still be present in the reservoir, either in a pool or by being trapped in interstices of relatively porous rock, it is necessary to effect the recovery of the petroleum by a tertiary method. The tertiary method or the enhanced oil recovery method may be effected by many different methods. For example, one tertiary recovery method may be thermal in nature in which steam is pumped into the reservoir to force the oil to the surface. However, some oil may be lost due to burning and, by combining the cost of the lost oil with the cost of the equipment and energy necessary to form the steam, may render such a method economically unattractive to operate. A second tertiary recovery method may comprise a fire flood method in which a portion of oil is ignited to create gases as well as reducing the viscosity of the heavy crude with a concomitant increase in pressure to force the oil from the reservoir. However, as in the method previously discussed, the drawback to this method is in the fact that some of the assets are being destroyed, thus increasing the cost of the operation. A third method for enhanced oil recovery is in the use of carbon dioxide to provide the pressure required to force the oil to the surface. In this method, the carbon dioxide is pumped into the oil reservoir to dissolve some of the heavies present which, in turn, will reduce the viscosity and allow the oil to reach the surface. The disadvantage which is present when utilizing such a method is the requirement for relatively expensive equipment to produce the carbon dioxide. In addition, the method is dependent upon the ready availability of carbon dioxide. Yet another method for enhanced oil recovery is found in the use of chemicals such as water-soluble polymers including polyacrylamide, bispolymers, etc. These polymers will increase the viscosity of the water in the solution and render the mobility ratio of water to oil whereby the solution will act more favorably as a plug.

Another method of effecting an enhanced oil recovery is by utilizing surfactants as a plug, whereby the oil which is present in the reservoir may be recovered by injecting an aqueous fluid containing a surfactant or a combination of surfactants along with other compounds into the reservoir. The use of surfactants in this system is necessary inasmuch as water alone does not displace petroleum with a relatively high degree of efficiency. This occurs due to the fact that water and oil are relatively immiscible and, in addition, the interfacial tension between water and oil is relatively high. The use of surfactants will lower or reduce the interfacial tension between the water and the oil, thus reducing the force which retains the oil which has been displaced in capillaries.

The prior art is replete with various surfactants which have been used in this tertiary system for the recovery of petroleum. One type of surfactant which has been employed in many processes involves a petroleum sulfonate. The sulfonate petroleum fractions have been obtained by sulfonating a crude oil. However, this crude oil feedstock contains a vast and varied number of chemical structures including aromatic hydrocarbons, paraffinic hydrocarbons, olefinic hydrocarbons, to name a few. However, a disadvantage in utilizing crude oil as a feedstock is that the feedstock usually does not contain a major portion of aromatic compounds which are the effective material which is sulfonated. As will hereinafter be shown, by utilizing certain linear alkylbenzene sulfonates which have been prepared from certain linear alkenes utilizing a specific type of catalyst, it is possible to obtain products which possess the desired physical characteristics necessary for lowering the interfacial tension between oil and water when used as one component of a surfactant slug.

As was previously discussed, prior U.S. patents teach the use of these petroleum sulfonates as one component of a surfactant mixture which may be used in a surfactant oil recovery process. For example, U.S. Pat. No. 4,214,999 discloses a surfactant fluid for use in flooding subterranean formations which contain petroleum comprising petroleum sulfonates possessing certain average equivalent weights and a solubilizing co-surfactant such as ethoxylated alkanols, sulfates or sulfonates. U.S. Pat. No. 4,013,569 also discloses a surfactant system for the recovery of petroleum utilizing a relatively water-soluble aromatic ester polysulfonate as one component in the system. Another U.S. patent, namely U.S. Pat. No. 4,008,165 utilizes an aqueous surfactant-containing fluid which includes a mixture of three surfactant materials including a sulfonate surfactant derived from an alkyl or alkylaromatic radical along with a phosphate ester surfactant and a sulfonated betaine, the system also being utilized in an oil recovery process.

BRIEF SUMMARY OF THE INVENTION

This invention relates to a process for the recovery of petroleum from subterranean reservoirs. More specifically, the invention is concerned with an enhanced oil recovery process in which petroleum, which is present in a subterranean reservoir, is recovered by utilizing a surfactant slug containing, as one component thereof, a soluble sulfonate of powdered coal which possesses certain physical characteristics.

As hereinbefore set forth, the recovery of petroleum from reservoirs must be accomplished in a commercial manner which is economically viable to operate. It is necessary, in many instances, to insure the complete recovery of petroleum from a particular reservoir in order to justify the expenditures which have been made in locating, drilling, etc. the particular reservoir. After recovery of the petroleum by primary means, such as natural forces of pressure as from an underlying water drive of gas dissolved in the petroleum which can exert a sufficient amount of pressure within the formation to force the petroleum up the well and to the surface, a secondary means of recovery may be expended. This supplemental recovery process may be accomplished by water flooding in which water is injected into the subterranean reservoir or formation. Following this, a tertiary or enhanced oil recovery system may be employed to further recover additional amounts of petroleum still present in the formation.

It is therefore an object of this invention to provide a process for the enhanced recovery of oil.

A further object of this invention is found in a process for the enhanced recovery of oil utilizing a surfactant slug containing a particular compound which acts as a surfactant for lowering the interfacial tension between the petroleum and water.

In one aspect, an embodiment of this invention resides in a process for enhanced oil recovery wherein an aqueous surfactant slug is introduced into a subterranean reservoir of oil to displace said oil from said reservoir, the improvement which comprises utilizing as one component of said slug a soluble sulfonate of powdered coal.

A specific embodiment of this invention is found in a process for enhanced oil recovery utilizing a surfactant slug for reducing the interfacial tension between oil and water, said slug comprising a soluble sulfonate of powdered coal, a lower alkyl alcohol containing from about 3 to about 6 carbon atoms and a non-ionic surfactant comprising an ethoxylated n-alcohol containing from about 12 to about 15 carbon atoms.

Other objects and embodiments will be found in the following further detailed description of the present invention.

DETAILED DESCRIPTION OF THE INVENTION

As hereinbefore set forth, the present invention is concerned with a surfactant slug which is used in an enhanced oil recovery process, said slug utilizing as one component thereof a soluble sulfonate which has been prepared by sulfonating powdered coal. As was previously discussed, the surfactant slugs which have been used in enhanced oil recovery processes contain, as one of the components of the slug, a sulfonated petroleum fraction. However, in contradistinction to this, the soluble sulfonates, which have been prepared by sulfonating powdered coal, which are utilized in the surfactant slug of the present invention will enable the finished slug to possess the desired physical characteristics so that the system can lower the interfacial tension between the oil which is present in the subterranean reservoir and water to values of the magnitude of $10^{-3}$ dynes per cm, thus making the system commercially attractive to use in the aforesaid enhanced oil recovery. This is especially true inasmuch as the soluble sulfonate of powdered coal may be prepared and obtained at a relatively low cost due to the ready availability of coal. In addition to possessing a relatively low interfacial tension, the surfactant slug will also possess the advantage of being able to tolerate the presence of sodium chloride which is usually present in the brine solution and which tends to precipitate out the sulfonates, especially the sulfonates which have been derived from petroleum. This precipitation of petroleum sulfonates will decrease the ability of the sulfonate to act as a surfactant for reducing the interfacial tension between the oil and water. Other advantages of the sulfonates of powdered coal lie in the tolerances of the sulfonate for calcium and magnesium, and by preventing the exchange of the sodium ions which have been used to neutralize the sulfonate with the subsequent precipitation hereinbefore discussed, as well as the advantage of possessing a relatively good solubility of the sulfonate in water.

As hereinbefore set forth, the aqueous surfactant slug which is utilized in the process for the enhanced recovery of oil from a subterranean reservoir comprises an admixture of a soluble sulfonate which has been obtained from powdered coal along with a co-surfactant and a ethoxylated normal alcohol. The sulfonates which are obtained from powdered coal may be prepared in any suitable manner from any coal source either bituminous or anthracite in nature, the latter type of coal being preferred. The coal is ground to the desired size by conventional means such as ball milling or any other means known in the art until a particular particle size has been attained. In the preferred embodiment of the invention, the coal is powdered until a particle size in the range of from about 5 to about 200 Tyler standard mesh size has been attained.

The sulfonate of the powdered coal may be prepared by treating the powdered coal in an appropriate reaction flask with a sulfonating agent such as sulfur trioxide or sulfuric acid in the presence, if so desired, of an organic solvent which may include paraffins such as pentane, hexane, heptane, etc., and cycloparaffins such as cyclopentane, methylcyclopentane, cyclohexane, etc. As one example of a sulfonation process, the powdered coal may be charged to a reaction flask along with the desired solvent and thereafter charging liquid sulfur trioxide under a nitrogen blanket to the reaction apparatus. The addition of the sulfur trioxide to the powdered coal may be effected at ambient temperature or temperatures slightly in excess of ambient, that is, up to about 50° C. over a relatively long period which may range from 1 to 10 hours or more in duration. Upon completion of the desired reaction period, the mixture may then be neutralized by the addition of an alkaline component of the type hereinbefore set forth in greater detail until an alkaline pH in excess of 7 is reached, thereafter water is added to the reaction mixture along with an equal amount of an alcohol such as isopropyl alcohol. After thorough agitation, the mixture is then heated to a temperature in the range of from about 50° C. to about 75° C. for a predetermined period of time and thereafter allowed to cool. The alkaline sulfonate which separates upon cooling is then removed by conventional means such as filtration, centrifugation, etc. and after the mixture is allowed to settle, it will separate into two layers. The lower aqueous/alcohol layer may then be extracted with an organic solvent such as hexane until the extracts are not colored. The upper organic layer along with the combined extracts may then be washed with water which is added to the aqueous layer. Thereafter, the aqueous layer is allowed to evaporate to dryness or a drying means such as a steam bath is used to yield the neutralized sulfonate derivative of the powdered coal. Inasmuch as coal, which contains a wide variety of chemical compounds, is highly aromatic in nature, the sulfonated compounds which are the result of the sulfonation of the coal will be useful in decreasing the interfacial tension between petroleum and water, that is, as hereinbefore set forth, permitting the surfactant slug to possess an interfacial tension property of less than $10^{-3}$ dynes/cm.

A second component of the surfactant slug will comprise a co-surfactant, said co-surfactant consisting of a lower alkyl alcohol containing from about 3 to about 6 carbon atoms such as n-propyl alcohol, isopropyl alcohol, n-butyl alcohol, sec-butyl alcohol, n-amyl alcohol, sec-amyl alcohol, n-hexyl alcohol, sec-hexyl alcohol, etc.

It is also contemplated within the scope of this invention that a third component of the surfactant slug will comprise a non-ionic surfactant comprising an ethoxylated normal alcohol containing from about 12 to about 15 carbon atoms in length. Specific examples of these alcohols will include ethoxy-n-dodecyl alcohol, ethoxy-n-tridecyl alcohol, ethoxy-n-tetradecyl alcohol, ethoxy-n-pentadecyl alcohol, etc. The amounts of the three components of the surfactant slug will usually comprise from about 1 to about 10% of the neutralized sulfonate of the powdered coal, from about 1 to about 10% of the lower alcohol co-surfactant, and from about 0.1 to about 2% of the non-ionic ethoxylated n-alcohol surfactant. In addition, if so desired, it is also contemplated within the scope of this invention that sodium chloride may also be present in an amount in the range of from about 1 to about 5%. However, the presence of this salt is not essentially necessary for the operation of the surfactant slug in lowering the interfacial tension between the petroleum and the slug.

By utilizing a surfactant slug containing the components hereinbefore described, it is possible to effect an enhanced oil recovery in which the petroleum which is still present in the subterranean reservoirs may be displaced from the reservoir and from the interstices of relatively porous rocks also present in an economically attractive manner.

The surfactant slug or system of the present invention may be formulated by admixing a predetermined amount of the aforesaid neutralized sulfonate derivative of the powdered coal, the cosurfactant and the non-ionic surfactant, said amounts being mixed in a water medium.

The water medium which is selected for the surfactant slug will usually consist of field water which, in many instances, comprises a low gravity brine. The thus prepared surfactant slug is then utilized for a tertiary method of enhanced oil recovery. In effecting the enhanced oil recovery process, the subterranean reservoir containing the oil may be subjected to a pre-flush treatment with fresh water in order to displace the water which has been used in the secondary process and which may possess a high degree of salinity and/or hardness from the flow channels of the formation. Following the pre-flush treatment, the surfactant slug is injected until the desired volume of surfactant fluid is present in the petroleum-containing formation. The surfactant slug, due to the presence of the various components including the sulfonates of powdered coal obtained by the thermal cracking of coal, will lower the interfacial tension between the oil and the water and thus assist in forcing the oil through the formation into the wells and through the wells to the surface for recovery thereof. Following the recovery of the oil, a further water injection is made into the formation, this water being sufficient to displace the surfactant and displaced oil so that the recovery of the oil is effected in such an amount as to render the process economically feasible.

The following examples are given for purposes of illustrating the preparation of a sulfonate of a powdered coal. However, it is to be understood that these examples are merely illustrative in nature and that the present process is not necessarily limited thereto.

EXAMPLE I

A feedstock comprising 50 grams of Illinois No. 6 coal which had been powdered to a particle size of 100/200 mesh along with 300 ml of hexane solvent was placed in a reactor provided with a mechanical stirrer, thermometer, reflux condenser and a gas inlet tube. Following this, 20 ml of liquid sulfur trioxide was placed in a separate bubbler apparatus. Nitrogen lines were attached to the gas inlet tube of the reaction flask and the inlet tube of the gas bubbler, while the outlet tube of the gas bubbler was connected to the gas inlet tube of the reaction flask. Nitrogen was charged at a sufficient rate in order to insure that the sulfur trioxide was delivered to the reaction flask as a 5–10% gaseous component of the nitrogen stream. The addition of the sulfur trioxide was accomplished during a period of 30 minutes, while maintaining the reaction temperature in a range of from about 25° to about 35° C.

At the end of the 30 minute period, the nitrogen was allowed to pass over the reaction mixture for an additional period of 1 hour following which the mixture was then extracted 3 times with 100 ml of an aqueous solution of isopropyl alcohol. The reaction mixture was filtered and the aqueous extract containing the soluble sulfonate of the powdered coal was recovered. The aqueous extract (40.0 grams) was placed in a reaction flask and neutralized to a pH of about 8 utilizing a solution containing 50% by weight of sodium hydroxide. In addition, about 50 ml of water which was equivalent to the volume of the reaction mixture was added followed by an equal amount of isopropanol. The mixture was then heated to a temperature of 80°–90° C. in a steam bath following which the flask was removed and placed in a refrigerator where it was allowed to cool. The sodium sulfate which separated upon cooling was recovered by suction filtration and the solid was washed with aqueous isopropanol. The filtrated washings, upon standing, separated into two layers, the upper organic layer being a mixture of oil and hexane, while the lower layer was a mixture of an aqueous solution and isopropyl alcohol. The lower aqueous layer was extracted with hexane following which the combined extracts and original upper layer were washed with water which was then added to the aqueous layer. The aqueous layer was evaporated to dryness utilizing a steam bath, the solids which comprised sodium sulfonate derivatives of the powdered coal were recovered.

EXAMPLE II

In a manner similar to that set forth in Example I above, 50 grams of Illinois No. 6 coal which had been ground to a particle size of 100/200 mesh was placed in a reaction flask similar to that utilized above along with 100 ml of decalin. A gas bubbler which contained 20 ml (36.8 grams) of liquid sulfur trioxide was attached to the reaction flask along with a nitrogen source. Sulfur trioxide was allowed to pass into the mixture of coal and diluent in a 5–10% gaseous component of a nitrogen flow for a period of 30 minutes while maintaining the termperature of the reaction in a range of from about 40° to about 70° C. At the end of the 30 minute period, during which time all of the sulfur trioxide was added, the flask was purged for an additional period of time with nitrogen. The reaction mixture was recovered and treated in a manner similar to that hereinbefore set forth to recover the sulfonate derivative of the powdered coal.

We claim:

1. A process for enhanced oil recovery from a subterranean reservoir of oil by injecting into said reservoir an aqueous surfactant slug to enhance displacement of said oil from said reservoir, said aqueous surfactant slug comprising from about 1 to about 10 weight percent of a neutralized sulfonate of powdered coal prepared by:
   (a) grinding a coal source to a particle size in the range of from about 5 to about 200 Tyler standard mesh;
   (b) treating said ground coal of step (a) with a sulfonating agent selected from the group consisting of sulfur trioxide and sulfuricacid at a temperature in the range of from about ambient to about 50° C. to produce a sulfonated powdered coal;
   (c) neutralizing said sulfonated powdered coal by adding an alkaline component at a temperature in the range of from about 50° C. to about 75° C. for a period of time to raise the pH of said sulfonated powdered coal to in excess of 7 to produce a neutralized sulfonated powdered coal;
   (d) recovering said neutralized sulfonated powdered coal for injection to said subterranean reservoir in oil.

2. The process as set forth in claim 1 which said alkaline component is a compound selected from the group consisting of ammonium hydroxide and a salt or hydroxide of a metal of Group IA and IIA of the Periodic Table.

3. The process as set forth in claim 2 in which said metal is sodium.

4. The process as set forth in claim 2 in which said metal is potassium.

5. The process as set forth in claim 1 in which said aqueous surfactant slug contains as a second component thereof a lower alkyl alcohol which possesses from about 3 to about 6 carbon atoms.

6. The process as set forth in claim 5 in which said lower alkyl alcohol is isopropyl alcohol.

7. The process as set forth in claim 5 in which the lower alkyl alcohol is isoamyl alcohol.

8. The process as set forth in claim 5 in which said aqueous surfactant slug contains as a third component thereof a non-ionic surfactant.

9. The process as set forth in claim 8 in which said non-ionic surfactant comprises an ethoxylated n-alcohol which possesses from about 12 to about 15 carbon atoms.

* * * * *